US011130973B1

(12) United States Patent
Tong et al.

(10) Patent No.: US 11,130,973 B1
(45) Date of Patent: Sep. 28, 2021

(54) RECOMBINANT STRAIN FOR PRODUCING L-LACTIC ACID

(71) Applicants: COFCO (jilin) Bio-Chemical Technology CO., Ltd, Changchun (CN); Nutrition & Health Research Institute, Beijing (CN); COFCO BIOTECHNOLOGY CO., LTD., Bengbu (CN)

(72) Inventors: Yi Tong, Beijing (CN); Yi Li, Beijing (CN); Yuan Zhang, Beijing (CN); Bo Chen, Beijing (CN); Xiaoyan Wang, Beijing (CN); Tai An, Beijing (CN); Kai Yang, Beijing (CN)

(73) Assignees: COFCO (JILIN) BIO-CHEMICAL TECHNOLOGY CO., LTD, Changchun (CN); NUTRITION & HEALTH RESEARCH INSTITUTE, COFCO CORPORATION, Beijing (CN); COFCO BIOTECHNOLOGY CO., LTD.

( * ) Notice: Subject to any disclaimer, the term of this patent is extended or adjusted under 35 U.S.C. 154(b) by 0 days.

(21) Appl. No.: 17/136,985

(22) Filed: Dec. 29, 2020

(30) Foreign Application Priority Data

May 25, 2020 (CN) .......................... 202010445993.9
May 27, 2020 (CN) .......................... 202010463397.3

(51) Int. Cl.
| C12N 15/74 | (2006.01) |
| C12N 15/09 | (2006.01) |
| C12P 7/56 | (2006.01) |
| C12N 9/04 | (2006.01) |
| A61K 38/00 | (2006.01) |

(52) U.S. Cl.
CPC .............. *C12P 7/56* (2013.01); *C12N 9/0006* (2013.01); *C12N 15/746* (2013.01); *C12Y 101/01027* (2013.01); *C12Y 101/01028* (2013.01)

(58) Field of Classification Search
CPC combination set(s) only.
See application file for complete search history.

(56) References Cited

U.S. PATENT DOCUMENTS

| 10,563,271 B2* | 2/2020 | Solem | C12N 1/205 |
| 2016/0130618 A1* | 5/2016 | Hara | C12P 13/04 |
| | | | 435/107 |
| 2018/0073045 A1* | 3/2018 | Wang | C12R 1/19 |

FOREIGN PATENT DOCUMENTS

| CN | 101880696 A | 11/2010 |
| CN | 109628339 A | 4/2019 |
| CN | 110272858 A | 9/2019 |

OTHER PUBLICATIONS

Kim et al. (1991) Cloning and Nucleotide Sequence of the Lactobacillus casei Lactate Dehydrogenase Gene (1991) Appl. Environ. Microbiol., vol. 57, No. 8, pp. 2413-2417.*
Ferain et al.( 1994) Lactobacillus plantarum ldhL Gene: Overexpression and Deletion Thierry Ferain, Dominique Garmyn, Nathalie Bern, J. Bacteriol., vol. 176, No. 3, pp. 596-661.*
Toh et al. (2013) Genomic Adaptation of the Lactobacillus casei Group, PLoS One, vol. 8, issue 10, e75073, pp. 1-11.*
Zhao, X. et al. "Homfermentative Production of Pure L-lactic Acid by Genetic Engineered *Escherichia coli*" (2012) Food and Fermentation Technology 48(5): 41-45.

* cited by examiner

*Primary Examiner* — Scarlett Y Goon
*Assistant Examiner* — Samuel W Liu
(74) *Attorney, Agent, or Firm* — Volpe Koenig

(57) ABSTRACT

The present disclosure relates to the technical fields of genetic engineering and microbial fermentation, and discloses a recombinant strain for producing L-lactic acid, wherein the recombinant strain is obtained by genetically modifying a starting strain, the activity of D-lactate dehydrogenase of the recombinant strain is weakened or inactivated, and the activity of L-lactate dehydrogenase is enhanced, as compared with the starting strain. The present invention can significantly improve the fermentation effect, the yield of the L-lactic acid and the optical purity of the product L-lactic acid.

3 Claims, No Drawings

Specification includes a Sequence Listing.

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1
atgagctcgg caccttgaac agtgtaacca                                         30

<210> SEQ ID NO 2
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 2
ccactgcaat acgattgacc tttttcatat tctcaatatc tccttgattt cgatttgtcc        60

<210> SEQ ID NO 3
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 3
ggacaaatcg aaatcaagga gatattgaga atatgaaaaa ggtcaatcgt attgcagtgg       60

<210> SEQ ID NO 4
<211> LENGTH: 55
<212> TYPE: DNA
<213> ORGANISM: Artificial Sequence
<220> FEATURE:
<223> OTHER INFORMATION: Synthetic Sequence

<400> SEQUENCE: 4
tgcttatttt tgcagcttaa aggatcctta caatacaggt gccatcgttt ctttt            55

<210> SEQ ID NO 5
<211> LENGTH: 55
<212> TYPE: DNA
<213> ORGANISM: Artificial Sequence
<220> FEATURE:
<223> OTHER INFORMATION: Synthetic Sequence

<400> SEQUENCE: 5
aaaagaaacg atggcacctg tattgtaagg atcctttaag ctgcaaaaat aagca            55
```

<210> SEQ ID NO 6
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 6
atgcatgcag actcagctct tggcggcctt t                               31

<210> SEQ ID NO 7
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 7
ggtgatcctt atccgtaata cttgccatat tctcaatatc tccttgattt cgatttgtcc    60

<210> SEQ ID NO 8
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 8
ggacaaatcg aaatcaagga gatattgaga atatggcaag tattacggat aaggatcacc    60

<210> SEQ ID NO 9
<211> LENGTH: 53
<212> TYPE: DNA
<213> ORGANISM: Artificial Sequence
<220> FEATURE:
<223> OTHER INFORMATION: Synthetic Sequence

<400> SEQUENCE: 9
tgcttatttt tgcagcttaa aggatcctta ctgacgggtt tcgatgtcgt tct           53

<210> SEQ ID NO 10
<211> LENGTH: 53
<212> TYPE: DNA
<213> ORGANISM: Artificial Sequence
<220> FEATURE:
<223> OTHER INFORMATION: Synthetic Sequence

<400> SEQUENCE: 10
agaacgacat cgaaacccgt cagtaaggat cctttaagct gcaaaaataa gca           53

<210> SEQ ID NO 11
<211> LENGTH: 312
<212> TYPE: PRT
<213> ORGANISM: Bacillus coagulans

<400> SEQUENCE: 11

Met Lys Lys Val Asn Arg Ile Ala Val Val Gly Thr Gly Ala Val Gly
1               5                   10                  15

Thr Ser Tyr Cys Tyr Ala Met Ile Asn Gln Gly Val Ala Glu Glu Leu
            20                  25                  30

Val Leu Ile Asp Ile Asn Glu Ala Lys Ala Glu Gly Glu Ala Met Asp
        35                  40                  45

Leu Asn His Gly Leu Pro Phe Ala Pro Thr Pro Thr Arg Val Trp Lys
    50                  55                  60

Gly Asp Tyr Ser Asp Cys Gly Thr Ala Asp Leu Val Val Ile Thr Ala
 65                  70                  75                  80

Gly Ser Pro Gln Lys Pro Gly Glu Thr Arg Leu Asp Leu Val Ala Lys
             85                  90                  95

Asn Ala Lys Ile Phe Lys Gly Met Ile Lys Ser Ile Met Asp Ser Gly
            100                 105                 110

Phe Asn Gly Ile Phe Leu Val Ala Ser Asn Pro Val Asp Ile Leu Thr
            115                 120                 125

Tyr Val Thr Trp Lys Glu Ser Gly Leu Pro Lys Glu His Val Ile Gly
        130                 135                 140

Ser Gly Thr Val Leu Asp Ser Ala Arg Leu Arg Asn Ser Leu Ser Ala
145                 150                 155                 160

His Phe Gly Ile Asp Pro Arg Asn Val His Ala Ala Ile Ile Gly Glu
                165                 170                 175

His Gly Asp Thr Glu Leu Pro Val Trp Ser His Thr Thr Ile Gly Tyr
            180                 185                 190

Asp Thr Ile Glu Ser Tyr Leu Gln Lys Gly Thr Ile Asp Gln Lys Thr
        195                 200                 205

Leu Asp Asp Ile Phe Val Asn Thr Arg Asp Ala Ala Tyr His Ile Ile
    210                 215                 220

Glu Arg Lys Gly Ala Thr Phe Tyr Gly Ile Gly Met Ser Leu Thr Arg
225                 230                 235                 240

Ile Thr Arg Ala Ile Leu Asn Asn Glu Asn Ser Val Leu Thr Val Ser
                245                 250                 255

Ala Phe Leu Glu Gly Gln Tyr Gly Asn Ser Asp Val Tyr Ile Gly Val
            260                 265                 270

Pro Ala Val Ile Asn Arg Gln Gly Val Arg Glu Val Val Glu Ile Glu
        275                 280                 285

Leu Asn Asp Lys Glu Gln Glu Gln Phe Ser His Ser Val Lys Val Leu
    290                 295                 300

Lys Glu Thr Met Ala Pro Val Leu
305                 310

<210> SEQ ID NO 12
<211> LENGTH: 939
<212> TYPE: DNA
<213> ORGANISM: Bacillus coagulans

<400> SEQUENCE: 12
atgaaaaagg tcaatcgtat tgcagtggtt ggaacgggtg cagttggtac aagttactgc      60
tacgccatga ttaatcaggg tgttgcagaa gagcttgttt taatcgatat taacgaagca     120
aaagcagaag gggaagccat ggacctgaac cacggcctgc catttgcgcc tacgccgacc     180
cgcgtttgga aaggagatta ttccgattgc ggcactgccg atcttgttgt cattacggca     240
ggttccccgc aaaaaccggg cgaaacaagg cttgatcttg ttgccaaaaa cgcaaaaatt     300
tttaaaggca tgattaagag catcatggac agcggcttta cgggattttt cttgttgcc      360 agcaacccgg ttgacatttt gacatatgta acttggaaag agtccggcct gccgaaagaa     420
catgttatcg gttcgggcac agtgcttgac tccgcgcgtc tccgcaactc tttgagcgcc     480
cacttcggaa ttgacccgcg caatgtccat gccgcaatta tcggcgaaca cggcgacacg     540
gaacttccgg tttggagcca tacaacgatc ggttatgaca ccattgaaag ctatctgcaa     600
aagggaacca ttgaccaaaa aacattagat gatatttttg tcaacacgag agatgcggct     660

```
taccatatca ttgaacgaaa aggggccaca ttttacggca tcgggatgtc tctgactcgg      720
atcacaagag cgatcctgaa caatgaaaac agtgttttga cagtctctgc cttttttggaa     780
```

```
taccatatca ttgaacgaaa aggggccaca ttttacggca tcgggatgtc tctgactcgg      720
atcacaagag cgatcctgaa caatgaaaac agtgttttga cagtctctgc cttttttggaa     780 ggccagtacg gaaacagcga tgtgtacatt ggtgttcctg ccgttattaa ccgccaaggc      840
gtccgtgaag tggttgaaat cgagctgaac gacaaagaac aggaacaatt tagccattct      900
gttaaagtat taaagaaac gatggcacct gtattgtaa                              939
```

<210> SEQ ID NO 13
<211> LENGTH: 326
<212> TYPE: PRT
<213> ORGANISM: Lactobacillus casei

<400> SEQUENCE: 13

```
Met Ala Ser Ile Thr Asp Lys Asp His Gln Lys Val Ile Leu Val Gly
1               5                   10                  15

Asp Gly Ala Val Gly Ser Ser Tyr Ala Tyr Ala Met Val Leu Gln Gly
                20                  25                  30

Ile Ala Gln Glu Ile Gly Ile Val Asp Ile Phe Lys Asp Lys Thr Lys
            35                  40                  45

Gly Asp Ala Ile Asp Leu Ser Asn Ala Leu Pro Phe Thr Ser Pro Lys
        50                  55                  60

Lys Ile Tyr Ser Ala Glu Tyr Ser Asp Ala Lys Asp Ala Asp Leu Val
65                  70                  75                  80

Val Ile Thr Ala Gly Ala Pro Gln Lys Pro Gly Glu Thr Arg Leu Asp
                85                  90                  95

Leu Val Asn Lys Asn Leu Lys Ile Leu Lys Ser Ile Val Asp Pro Ile
            100                 105                 110

Val Asp Ser Gly Phe Asn Gly Ile Phe Leu Val Ala Ala Asn Pro Val
        115                 120                 125

Asp Ile Leu Thr Tyr Ala Thr Trp Lys Leu Ser Gly Phe Pro Lys Asn
130                 135                 140

Arg Val Val Gly Ser Gly Thr Ser Leu Asp Thr Ala Arg Phe Arg Gln
145                 150                 155                 160

Ser Ile Ala Glu Met Val Asn Val Asp Ala Arg Ser Val His Ala Tyr
                165                 170                 175

Ile Met Gly Glu His Gly Asp Thr Glu Phe Pro Val Trp Ser His Ala
            180                 185                 190

Asn Ile Gly Gly Val Thr Ile Ala Glu Trp Val Lys Ala His Pro Glu
        195                 200                 205

Ile Lys Glu Asp Lys Leu Val Lys Met Phe Glu Asp Val Arg Asp Ala
210                 215                 220

Ala Tyr Glu Ile Ile Lys Leu Lys Gly Ala Thr Phe Tyr Gly Ile Ala
225                 230                 235                 240

Thr Ala Leu Ala Arg Ile Ser Lys Ala Ile Leu Asn Asp Glu Asn Ala
                245                 250                 255

Val Leu Pro Leu Ser Val Tyr Met Asp Gly Gln Tyr Gly Leu Asn Asp
            260                 265                 270

Ile Tyr Ile Gly Thr Pro Ala Val Ile Asn Arg Asn Gly Ile Gln Asn
        275                 280                 285

Ile Leu Glu Ile Pro Leu Thr Asp His Glu Glu Ser Met Gln Lys
290                 295                 300

Ser Ala Ser Gln Leu Lys Lys Val Leu Thr Asp Ala Phe Ala Lys Asn
305                 310                 315                 320

Asp Ile Glu Thr Arg Gln
```

<210> SEQ ID NO 14
<211> LENGTH: 981
<212> TYPE: DNA
<213> ORGANISM: Lactobacillus casei

<400> SEQUENCE: 14

```
atggcaagta ttacggataa ggatcaccaa aaagttattc tcgttggtga cggcgccgtt      60
ggttcaagtt atgcctatgc aatggtattg caaggtattg cacaagaaat cgggatcgtt     120
gacatttta aggacaagac gaagggtgac gcgattgact tatcgaacgc gctgccattc     180
accagcccaa agaagattta ttcagctgaa tacagcgatg ccaaggatgc tgatctggtt     240
gttatcactg ctggtgctcc tcagaagcca ggcgaaaccc gcttggatct ggttaacaag     300
aacttgaaga tcttgaagtc cattgttgat ccgattgtgg attctggctt taacggtatc     360
ttcttggttg ctgccaaccc agttgatatc ttgacctatg caacttggaa actttccggc     420
ttcccgaaga accgggttgt tggttcaggt acttcattgg ataccgcacg tttccgtcag     480
tccattgctg aaatggttaa cgttgatgca cgttcggtcc atgcttacat catgggtgaa     540
catggtgaca ctgaattccc tgtatggtca cacgctaaca tcggtggcgt tactattgcc     600
gaatgggtta aagcacatcc ggaaatcaag gaagacaagc ttgttaagat gtttgaagac     660
gttcgtgacg ctgcttacga aatcatcaaa ctcaagggcg caaccttcta tggtatcgca     720
actgctttgg cacgtatctc caaggctatc ctgaacgatg aaaatgctgt tctgccactg     780
tccgtttaca tggatggtca atatggcttg aacgacatct acatcggtac cccagctgtg     840
atcaaccgaa atggtatcca gaacattctg gaaattccat tgaccgacca cgaagaggaa     900
tccatgcaga atctgcttc acaattgaag aaggttctga ctgatgcctt cgcgaagaac     960
gacatcgaaa cccgtcagta a                                               981
```

<210> SEQ ID NO 15
<211> LENGTH: 333
<212> TYPE: PRT
<213> ORGANISM: Lactobacillus rhamnosus

<400> SEQUENCE: 15

```
Met Lys Ile Ile Ala Tyr Gly Ala Arg Val Asp Glu Ile Gln Tyr Phe
1               5                   10                  15

Lys Gln Trp Ala Lys Glu Thr Gly Asn Thr Leu Glu Tyr His Thr Glu
            20                  25                  30

Phe Leu Asp Glu His Thr Val Glu Trp Ala Lys Gly Phe Asp Gly Ile
        35                  40                  45

Asn Ser Leu Gln Thr Thr Pro Tyr Ala Ala Gly Val Phe Glu Lys Met
    50                  55                  60

His Glu Tyr Gly Ile Lys Phe Leu Thr Ile Arg Asn Val Gly Thr Asp
65                  70                  75                  80

Asn Ile Asp Met Thr Ala Met Lys Lys Tyr Gly Ile Arg Leu Ser Asn
                85                  90                  95

Val Pro Ala Tyr Ser Pro Ala Ala Ile Ala Glu Phe Ala Leu Thr Asp
            100                 105                 110

Thr Leu Tyr Leu Leu Arg Asn Met Gly Lys Val Gln Ala Gln Leu His
        115                 120                 125

Ala Gly Asp Tyr Glu Lys Ala Ser Thr Phe Ile Gly Lys Glu Leu Gly
    130                 135                 140
```

```
Gln Gln Thr Val Gly Val Met Gly Thr Gly His Ile Gly Arg Val Ala
145                 150                 155                 160

Ile Lys Leu Phe Lys Gly Phe Gly Ala Lys Val Ile Ala Tyr Asp Pro
                165                 170                 175

Tyr Pro Met Lys Gly Asp His Pro Asp Phe Glu Tyr Val Ser Leu Glu
            180                 185                 190

Glu Leu Phe Lys Gln Ser Asp Ile Ile Asp Leu His Val Pro Gly Ile
        195                 200                 205

Lys Gln Asn Thr His Ile Ile Asn Glu Ala Ala Phe Asp Leu Met Lys
    210                 215                 220

Pro Gly Ala Ile Val Ile Asn Thr Ala Arg Pro Asn Leu Ile Asp Thr
225                 230                 235                 240

Gln Ala Met Leu Ser Asn Leu Lys Ser Gly Lys Leu Ala Gly Val Gly
                245                 250                 255

Ile Asp Thr Tyr Glu Tyr Glu Thr Glu Asp Leu Leu Asn Leu Ala Lys
                260                 265                 270

His Gly Ser Phe Lys Asp Pro Leu Trp Asp Glu Leu Leu Ala Met Pro
            275                 280                 285

Asn Val Val Leu Ser Pro His Ile Ala Tyr Tyr Thr Glu Thr Ala Val
290                 295                 300

His Asn Met Val Tyr Phe Ser Leu Gln Asn Leu Val Asp Phe Leu Thr
305                 310                 315                 320

Arg Gly Glu Thr Asn Thr Glu Val Thr Ala Pro Ala Lys
                325                 330

<210> SEQ ID NO 16
<211> LENGTH: 1003
<212> TYPE: DNA
<213> ORGANISM: Lactobacillus rhamnosus

<400> SEQUENCE: 16
atgaagatta ttgcatatgg tgcacgcgtg gatgagatcc aatatttcaa acagtgggct      60
aaggaaaccg gcaacacgct ggaatatcat acggaatttc ttgatgagca taccgttgaa     120
tgggcaaagg gatttgacgg cattaactca ctacaaacga cgccatacgc agctggtgtg     180
tttgaaaaaa tgcacgaata tggcatcaag tttctcacca tccgcaatgt cggaaccgac     240
aatatcgata tgacggcgat gaaaaaatac ggcattcgct aagtaatgt tccggcgtat      300
tcaccggctg ccattgctga atttgcgcta accgatacgt tatatctact cgcaacatg      360
ggaaaggttc aagcacagct acatgcaggc gactacgaaa agccagcac cttcatcggc      420
aaagaacttg gtcagcaaac agtcggcgtg atggggaccg gacacattgg ccgcgttgcc     480
atcaagctct tcaaaggttt tggtgccaaa gtgattgctt acgatccata tccgatgaaa     540
ggcgatcatc cggactttga atatgtcagc ttggaagaac tattcaaaca aagtgacatc     600
attgatcttc acgttccggg cattaaacaa atacccaca ttatcaacga ggccgcgttt      660
gatcttatga agccaggcgc gatcgtaatt aacaccgcgc ggccgaacct gattgatacc     720
caggcgatgc tcagcaacct gaagtccggt aaactggccg gcgtcggaat cgatacgtac     780
gaatacgaaa ccgaagatct gttgaacctc gccaaacacg gtagcttcaa ggatccgtta     840
tgggatgaac tgctcgcgat gccaaatgtt gttctcagcc gcatattgc gtactacaca      900
gaaaaccgcc gtgcacaaca tggtttactt ctcactgcag aatttagtcg acttttttgac    960
aaggggagag acgaatactg aagtgacagc accggcgaaa taa                      1003
```

```
<210> SEQ ID NO 17
<211> LENGTH: 699
<212> TYPE: DNA
<213> ORGANISM: Artificial Sequence
<220> FEATURE:
<223> OTHER INFORMATION: Synthetic Sequence

<400> SEQUENCE: 17
atggctatta aaaatactaa agctagaaat tttggatttt tattatatcc tgactcaatt      60
cctaatgatt ggaaagaaaa attagagagt ttgggcgtat ctatggctgt cagtccttta     120
cacgatatgg acgaaaaaaa agataaagat acatggaata atagtaatat tatacaaaat     180
ggaaagcact ataaaaaacc acactatcac gttatatata ttgcacgaaa tcctgtaaca     240
atagaaagcg ttaggaacaa gattaagcga aaattgggga atagttcagt tgctcatgtt     300
gagatacttg attatatcaa aggttcatat gaatatttga ctcatgaatc aaaggacgct     360
attgctaaga ataaacatat atacgacaaa aaagatattt tgaacattaa tgattttgat     420
attgaccgct atataacact tgatgaaagc caaaaaagag aattgaagaa tttacttta      480 gatatagtgg atgactataa tttggtaaat acaaaagatt taatggcttt tattcgcctt     540
aggggagcgg agtttggaat tttaaatacg aatgatgtaa aagatattgt ttcaacaaac     600
tctagcgcct ttagattatg gtttgagggc aattatcagt gtggatatag agcaagttat     660
gcaaaggttc ttgatgctga aacgggggaa ataaaatga                            699
```

RECOMBINANT STRAIN FOR PRODUCING L-LACTIC ACID

PRIORITY CLAIM & CROSS REFERENCE

The application claims priority to Chinese Application No. 202010463397.3, filed on May 27, 2020, entitled "A recombinant strain for producing L-lactic acid, a construction method thereof and a method for producing L-lactic acid by fermentation and uses thereof", which is herein specifically and entirely incorporated by reference.

The application also claims priority to Chinese Application No. 202010445993.9, filed on May 25, 2020, entitled "*Lactobacillus rhamnosus* and method for producing L-lactic acid by fermentation and uses thereof", which is herein specifically and entirely incorporated by reference.

The Sequence Listing originally filed, titled "SEQUENCE LISTING," and having a file size of 15 KB is incorporated herein by reference as if fully set forth. The Sequence Listing filed Mar. 9, 2021, titled "SEQUENCE LISTING," and having a file size of 16 KB is incorporated herein by reference as if fully set forth.

FIELD

The present disclosure relates to the technical fields of genetic engineering and microbial fermentation, in particular to a recombinant strain for producing L-lactic acid.

BACKGROUND

Polylactic acid (PLA) is a biodegradable high-molecular polymer formed by condensation polymerization of lactic acid monomers, and is mainly obtained by polymerization reaction using L-lactic acid (i.e., a fermentation product of microorganisms) as the monomer. PLA is an ideal environmentally friendly polymer material because the raw material of PLA is a renewable biological resource, and is generally recognized as a novel "biobased material" by the industry. In addition, the product prepared from PLA has desirable glossiness, transparency, hand feeling and heat resistance, shows certain characteristics of bacterium resistance, flame retardance and ultraviolet resistance, and has high glossiness and processability; PLA also has the traits of being non-toxic, non-irritative, biocompatible and the like. Therefore, PLA has an expansive market prospect and wide application. At present, polylactic acid is mainly used in a plurality of fields such as clothing, architecture, agriculture, forestry, paper making, medical treatment and health care.

The polylactic acid is mainly consisting of poly(L-lactide) (PLLA), poly(D-lactide) (PDLA) and poly(DL-lactide) (PDLLA). Given that the humans and many mammals can only metabolize L-lactic acid, thus the L-lactic acid is exclusively used as a raw material for production or an additive of product in the food, pharmaceutical, veterinary and feed industries. More specifically, the polylactic acid material polymerized from the raw material of L-lactic acid with optical purity more than 98% has attracted attention from the people, and has more important significance for industrial and agricultural production and livelihood of the people. So far, L-lactic acid has been mainly prepared by chemical synthesis and microbial fermentation. The chemical synthesis method has the troublesome problems such as environmental pollution, high cost, complex technology and low optical purity, and is difficult to meet the requirements of practical application. In contrast, the microbial fermentation method for producing L-lactic acid by using renewable resources (e.g., glucose) as raw materials has the advantages of low production cost, high optical purity and safety of products, mild production conditions, low pollution and so forth, as a result, most of the industrial production of L-lactic acid all over the world is carried out by the microbial fermentation method at present. Most lactic acid bacteria produce both L-lactic acid and D-lactic acid, the yield and optical purity of L-lactic acid can hardly meet the practical demand.

At present, there are still very limited strains to be selected during the industrial mass production of L-lactic acid with the microbial fermentation method, and known production strains commonly used in the L-lactic acid fermentation production are *Bacillus coagulans*, *Lactobacillus casei*, and *Lactobacillus rhamnous*, among others. Therefore, it is required to further breed the high-yield strains and continuously discover new strains in order to achieve the goals of increased yield, improved purity, reduced cost, improved benefit and the like. The screening and modification of the lactic acid fermentation strains are mainly focused on three aspects as follows: obtaining a high-yield strain; selecting and breeding the environmental stress resistant strains; and constructing a transgenic engineering strain.

Among them, enhancing the resistance of lactic acid fermentation strains to environmental stress is one of the important means for improving lactic acid fermentation capability. The researches have demonstrated that the lactic acid yield and the product optical purity can be improved by enhancing the high sugar concentration resistance and the high calcium lactate concentration resistance of the *Lactobacillus lactis* strains; the yield and the biomass of the lactic acid of the *Lactobacillus rhamnosus* can be increased by improving the acid resistance and the sugar resistance thereof. In this regard, the high temperature resistant strain can bring about enormous advantages in the lactic acid fermentation industry, for example, the high temperature resistant strain can be utilized for generating the favorable effects of shortening the production period, reducing the energy consumption required by temperature control in the fermentation production, saving cooling water, and decreasing possibility of contamination by the miscellaneous bacteria. On the other hand, it is also an object consistently pursued by those skilled in the art to obtain the desirable and useful strain by modifying a high-producing strain with genetic engineering means to further improve the acid production efficiency or optical purity of the product.

For this reason, there is currently a great room for improvement in regard to the recombinant L-lactic acid-producing strains having high temperature resistance and being capable of producing L-lactic acid with high yield and optical purity.

SUMMARY

The present disclosure aims to overcome the problem in the art associated with low yield and optical purity of the L-lactic acid obtained by microbial fermentation, and provides a recombinant strain for producing L-lactic acid, wherein the recombinant strain producing L-lactic acid by fermentation has the advantages of high L-lactic acid yield and high optical purity of the product L-lactic acid, low fermentation cost, shortened production period, reduced energy consumption required by temperature control in fermentation production, saved cooling water, decreased contamination of miscellaneous bacteria and environmental friendliness.

In order to fulfill the above purpose, the present disclosure provides a recombinant strain for producing L-lactic acid, wherein the recombinant strain is obtained by genetically modifying a starting strain, the activity of D-lactate dehydrogenase of the recombinant strain is weakened or inactivated, and the activity of L-lactate dehydrogenase is enhanced, as compared with the starting strain.

Through the aforementioned technical solution, the present disclosure can effectively improve the yield of the L-lactic acid. Moreover, the present disclosure has the advantages of low fermentation cost, shortened production period, reduced energy consumption required by temperature control in fermentation production, saved cooling water, decreased contamination of miscellaneous bacteria and environmental friendliness.

In the most preferred embodiment of the present disclosure, the lactic acid contents in the fermentation liquor obtained by fermenting the recombinant *Lactobacillus rhamnosus* Lr-ALHTHT-DBC and the recombinant *Lactobacillus rhamnosus* Lr-ALHTHT-DLC for 48 h are 216 g/L and 215.3 g/L respectively, the glucose-lactic acid conversion rates are 97% and 96.5%, the optical purities of the L-lactic acid are 99.8% and 99.5%, such that the fermentation effect, and the yield of the L-lactic acid and the optical purity of the L-lactic acid product are more remarkably improved.

BIOLOGICAL DEPOSITION

The *Lactobacillus rhamnosus* Lr-ALTHT was deposited in China Committee for Culture Collection of Microorganisms's common micro-organisms center (CGMCC) (address: the Chaoyang District, Beijing City North Star west day The institute 3 of road 1, Institute of Microorganism, Academia Sinica) on Nov. 28, 2018, and the accession number was CGMCC No. 16834.

The *Lactobacillus rhamnosus* Lr-ALTHT-DBC was deposited in China General Microbiological Culture Collection Center (CGMCC) (address: No. 3, Courtyard 1, Beichen West Road, Chaoyang District, Beijing; Institute of Microbiology, Chinese Academy of Sciences, zip code: 100101) on Mar. 25, 2020, and the accession number was CGMCC No. 19507.

The *Lactobacillus rhamnosus* Lr-ALTHT-DLC was deposited in The China General Microbiological Culture Collection Center (CGMCC) (address: No. 3, Courtyard 1, Beichen West Road, Chaoyang District, Beijing; Institute of Microbiology, Chinese Academy of Sciences, zip code: 100101) on Mar. 25, 2020, and the accession number was CGMCC No. 19508.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The terms "increase", "enhancing", "strengthen" or "activate" used in the present disclosure generally mean an increase in a statistically significant amount. However, for the avoidance of doubt, the terms "increase", "enhancing", "strengthen" or "activate" refer to an increase by at least 10% compared to a reference level (e.g. a level in the starting strain), for example, an increase of at least about 20%, or at least about 30%, or at least about 40%, or at least about 50%, or at least about 60%, or at least about 70%, or at least about 80%, or at least about 90%, or up to and including 100%, or any amount between 10% and 100%, compared to a reference level; or increase at least about 2-fold, or at least about 3-fold, or at least about 4-fold, or at least about 5-fold, or at least about 10-fold increase, or any amount between 2-fold and 10-fold, or a larger amount, compared to a reference level.

The term "weaken" or "inactivate" used herein refers to a reduction in the catalytic reaction capability of an enzyme by at least about 80%, or at least about 90%, or at least about 95%, or at least about 98%, or at least about 99%, or the complete loss of the catalytic reaction capability.

In a first aspect, the present disclosure provides a recombinant strain producing L-lactic acid, wherein the recombinant strain is obtained by genetically modifying a starting strain, the activity of D-lactate dehydrogenase of the recombinant strain is weakened or inactivated, and the activity of L-lactate dehydrogenase is enhanced, as compared with the starting strain.

In the present disclosure, it is preferable that the starting strain is *Lactobacillus rhamnosus*, more preferably *Lactobacillus rhamnosus* with an accession number of CGMCC No. 16834, which has been disclosed in CN109628339A.

In the present disclosure, in order to improve the L-lactic acid yield of the recombinant strain and the optical purity of the product L-lactic acid, it is preferable that at least a part of the D-lactate dehydrogenase gene in the recombinant strain is knocked out. More preferably, the amino acid sequence encoded by the knocked-out D-lactate dehydrogenase gene is as set forth as SEQ ID NO: 15. Further preferably, the sequence of the knocked-out D-lactate dehydrogenase gene is as set forth as SEQ ID NO: 16. The inventors of the present disclosure have discovered that the knockout of D-lactate dehydrogenase gene encoding sequence as set forth as SEQ ID NO: 15 in the starting strain *Lactobacillus rhamnosus* CGMCC No. 16834 can significantly improve the optical purity of the fermentation product L-lactic acid.

And/or, the recombinant strain contains a gene encoding L-lactate dehydrogenase of *Bacillus coagulans* and/or a gene encoding L-lactate dehydrogenase of *Lactobacillus casei*.

The inventors of the present disclosure have found in researches that the productivity and optical purity of L-lactic acid can be further improved by knocking out at least a part of the D-lactate dehydrogenase gene in the recombinant strain, and including the gene encoding L-lactate dehydrogenase of *Bacillus coagulans* and/or the gene encoding L-lactate dehydrogenase of *Lactobacillus casei* in the recombinant strain.

Further preferably, at least a part of the D-lactate dehydrogenase gene in the recombinant strain is knocked out such that the knocked-out D-lactate dehydrogenase gene in the recombinant strain is substituted with the gene encoding L-lactate dehydrogenase of *Bacillus coagulans* and/or a gene encoding L-lactate dehydrogenase of *Lactobacillus casei*.

The knockout (i.e., gene knock-out) refers to a technique of integrating an exogenous gene at a fixed point into a certain site on the target cell genome by homologous recombination, so as to fulfill the purpose of decorating and modifying a certain gene on a chromosome at a fixed point.

In the present disclosure, it is preferable that the recombinant strain comprises a L-lactate dehydrogenase gene encoding an amino acid sequence as set forth as SEQ ID NO: 11 and/or SEQ ID NO: 13.

Preferably, the recombinant strain comprises a L-lactate dehydrogenase gene with a sequence as set forth as SEQ ID NO: 12 and/or SEQ ID NO: 14.

According to a preferred embodiment of the present disclosure, the recombinant strain has an accession number CGMCC No. 19507 or CGMCC No. 19508.

In a second aspect, the present disclosure provides a method for constructing a recombinant strain, wherein the method comprises: genetically modifying a starting strain, such that the activity of D-lactate dehydrogenase of the starting strain is weakened or inactivated, and the activity of L-lactate dehydrogenase of the starting strain is enhanced.

In the present disclosure, it is preferable that the starting strain is *Lactobacillus rhamnosus*, more preferably *Lactobacillus rhamnosus* with the accession number of CGMCC No. 16834, which has been disclosed in CN109628339A.

In the present disclosure, the way of weakening activity or inactivating the D-lactate dehydrogenase of the starting strain is preferably gene knock-out. More preferably, the amino acid sequence encoded by the knocked-out D-lactate dehydrogenase gene is as set forth as SEQ ID NO: 15. Further preferably, the sequence of the knocked-out D-lactate dehydrogenase gene is as set forth as SEQ ID NO: 16.

And/or, the way of enhancing activity of the L-lactate dehydrogenase of the starting strain is exogenously introducing the L-lactate dehydrogenase gene of *Bacillus coagulans* and/or the L-lactate dehydrogenase gene of *Lactobacillus casei*.

The inventors of the present disclosure have discovered in researches that the yield and the optical purity of the L-lactic acid can be further improved by genetically knocking out at least a part of D-lactate dehydrogenase genes in the recombinant strain and exogenously introducing the L-lactate dehydrogenase gene of *Bacillus coagulans* and/or the L-lactate dehydrogenase gene of *Lactobacillus casei*.

Further preferably, the gene of the knocked-out D-lactate dehydrogenase in the recombinant strain is substituted by a gene encoding the L-lactate dehydrogenase of *Bacillus coagulans* and/or a gene encoding the L-lactate dehydrogenase of *Lactobacillus casei* by genetically knocking out at least a part of the D-lactate dehydrogenase gene in the recombinant strain.

In the present disclosure, it is preferable to knock out a specific open reading frame sequence or promoter sequence in the *Lactobacillus rhamnosus* genome by means of gene knock-out.

In the present disclosure, the homologous sequence fragment used in the gene knock-out can be obtained through the following modes: the synthetic method was performed according to the upstream and downstream fragment sequences of the target gene (e.g., ldhD gene) in *Lactobacillus rhamnosus* disclosed in databases generally known in the technical field, such as GenBank database (https://www.ncbi.nlm.nih.gov/GenBank) as the homologous arm; or amplifying the upstream and downstream fragment sequences of the target gene from the genome of the starting strain (such as *Lactobacillus rhamnosus* CGMCC No. 16834) by using a PCR method and applying it as the homologous arm, thereby obtaining the initial homologous sequence fragment of the target gene, but the present disclosure is not limited thereto. A part or all of the original homologous sequence of the target gene refers to a sequence containing the target gene as described above. The exogenous gene sequence fragment used for homologous knock-in (relating to homologous knock-in such as the Bcldh gene of *Bacillus coagulans* and the LcldhL gene of *Lactobacillus casei*) can also be obtained through a similar manner, but the present disclosure is not limited thereto.

Homologous knock-in (i.e., gene knock-in), refers to a technique of obtaining expression in a cell by transferring an exogenous functional gene (a gene which does not exist in the target cell genome or has inactivated) into the cell, performing a homologous recombination with a homologous sequence in the cell genome, and inserting the recombined genes into the genome.

It is understandable that the target gene is knocked out simultaneously with the knocking-in of the exogenous gene sequence fragment.

In the present disclosure, a recombinant vector can be constructed firstly, the recombinant vector can knock out the D-lactate dehydrogenase gene of a starting strain (such as *Lactobacillus rhamnosus* CGMCC No. 16834), and the L-lactate dehydrogenase gene is introduced exogenously. The recombinant vector is reproducible in *Escherichia coli*, the reproduction in lactic acid bacteria is controlled by temperature, and has erythromycin and chloramphenicol resistance genes which can be used in the *Escherichia coli* and *Lactobacillus plantarum*, and chloramphenicol resistance genes which can be used in the *Escherichia coli* and *Lactobacillus rhamnosus*. There are a variety of methods of constructing recombinant vectors well-known in the art for ligating a gene fragment of interest to an expression vector to prepare a recombinant vector, the construction methods may be, but not limited to, the classical "enzyme digestion-ligation" method, the Gateway cloning system developed by the Invitrogen Corporation, the Creator cloning system developed by the Clontech Corporation, the Univector cloning system developed by the Stephen Elridge Laboratory, and the Golden Gate cloning method based on Type IIs restriction enzymes (for example, using the GeneArt Type IIs Assembly kit supplied by the Thermo Fisher Incorporation).

For example, the recombinant vectors of the present disclosure can be constructed using the recombinant enzyme method: based on the genome of a starting strain (e.g., *Lactobacillus rhamnosus* CGMCC No. 16834), amplifying by adopting a PCR method to obtain the upstream and downstream homologous arm sequences of a target insertion site; the gene sequence to be inserted, the upstream and downstream homologous arm sequences, the resistance gene expression cassette and the like are connected in series to obtain a recombinant vector, but the present disclosure is not limited thereto.

The recombinant vector can then be introduced into the starting strain (e.g., *Lactobacillus rhamnosus* CGMCC No. 16834) using the conventional methods in the art, for example, but not limited to, microinjection, gene gun, transformation (e.g., electrotransformation), infection or transfection. Each of the microinjection, gene gun, transformation, infection or transfection is the conventional operation in the art. For example, transformation refers to treating cells by using some known method in molecular biology and genetic engineering to make the treated cell in a competent state, thereby contacting with an exogenous DNA, such that the exogenous DNA enters into the cell in a competent state. The commonly used transformation methods include protoplast transformation, chemical transformation, and electroporation conversion. Infection refers to using a live virus of an artificially modified bacteriophage as a vector, recombining the vector with a target DNA sequence, and packaging the recombinant DNA into a viable bacteriophage or virus in vitro using the coat protein of the bacteriophage or virus, thereby introducing the recombinant DNA into a host cell in an infectious manner. Transfection refers to treating cells into cells with a competent state by using $CaCl_2$), electroporation, or similar method, and then enabling the competent cells to accept the recombinant bacteriophage DNA.

After the recombinant vector is introduced into a starting strain (e.g., *Lactobacillus rhamnosus* CGMCC No. 16834), the positive clones can be screened out through a screening marker (e.g., a resistance gene), and verified through genome PCR or genome DNA sequencing, so as to obtain the recombinant strain producing L-lactic acid.

In the present disclosure, preferably, the way of enhancing activity of the L-lactate dehydrogenase of the starting strain is exogenously introducing a gene encoding an amino acid sequence as set forth as SEQ ID NO: 11 and/or SEQ ID NO: 13.

More preferably, the way of enhancing activity of the L-lactate dehydrogenase of the starting strain is exogenously introducing a gene with a sequence as set forth as SEQ ID NO: 12 and/or SEQ ID NO: 14.

In a third aspect, the present disclosure provides a method for producing L-lactic acid by fermentation, wherein the method comprises: inoculating the previously described recombinant strain into an acid-producing fermentation medium to perform a fermentation;
or, constructing the recombinant strain with the previously described method, and inoculating the obtained recombinant strain into an acid-producing fermentation culture medium to perform a fermentation.

In the present disclosure, preferably, the recombinant strain is prepared into a seed solution, and then the seed solution is inoculated into an acid-producing fermentation medium to perform a fermentation, so as to obtain a fermentation broth.

In the present disclosure, the $OD_{600}$ value of the seed solution reaches 5 or more, which indicates that the strain grows normally; for the sake of improving the fermentation effect, the $OD_{600}$ value in the seed solution is preferably within a range of 10-15.

Wherein the $OD_{600}$ refers to the light absorption value of the seed solution in a spectrophotometer at the wavelength of 600 nm.

In the present disclosure, it is preferable that the preparation method of the seed solution comprises: selecting a single colony of the recombinant strain, and inoculating the single colony into a seed culture medium for performing seed culture, in order to obtain the seed solution.

The present disclosure does not impose a specific limitation on the seed culture medium, which may be a seed culture medium conventionally used in the art for preparing *Lactobacillus rhamnosus* seed solution, and preferably, the seed culture medium is MRS liquid culture medium.

Preferably, the conditions of the seed culture include: the rotational speed is within a range of 100-180 rpm, and more preferably 120-150 rpm; the temperature is 37-40° C.; and the time is 12-24 h.

Preferably, the single colony of the recombinant strain may be selected from the group consisting of a freshly prepared recombinant strain or a cryopreserved recombinant strain (e.g., an L-lactic acid producing strain cryopreserved in a glycerol cryopreserved tube, e.g., in a −80° C. refrigerator).

The fermentation method is not particularly limited in the present disclosure, and may be a conventionally used method for producing L-lactic acid by fermentation in the art, such as inoculating the seed solution into the acid-producing fermentation medium (e.g., into a shake flask or a fermentation tank containing an acid-producing fermentation medium) to perform fermentation culture so as to obtain a fermentation broth.

In order to increase yield of the L-lactic acid, it is preferable in the present disclosure that the inoculation amount of the seed solution is 5 to 10 parts by volume relative to 100 parts by volume of the acid-producing fermentation medium.

In order to increase the yield of L-lactic acid, it is preferable in the present disclosure that the fermentation conditions include: firstly, fermenting for 4-6 h, preferably 5-6 h at the rotational speed of 100-180 rpm, preferably 120-150 rpm and the temperature of 37-40° C.; then fermenting for 40-44 h, preferably 42-44 h, at the rotational speed of 100-180 rpm, preferably 120-150 rpm, and the temperature of 42-48° C., more preferably 45-48° C., and further preferably 46-48° C., so as to obtain the fermentation broth.

In the present disclosure, it is preferable that the acid-producing fermentation medium comprises glucose, an organic nitrogen source (e.g. yeast extract), sodium acetate, phosphate, trace elements and a neutralizer.

More preferably, the acid-producing fermentation medium comprises, 160-200 g/L of glucose, 8-12 g/L of yeast extract, 1-3 g/L of sodium acetate, 0.3-0.7 g/L of $KH_2PO_4$, 0.5-1 g/L of $MgSO_4.7H_2O$, 0.1-0.2 g/L of $MnSO_4$, 0.5-1.5 ml/L of tween 80 (i.e., polysorbate 80) and a neutralizer, relative to 1 L of the acid-producing fermentation medium.

In the present disclosure, the weight ratio of the content of the neutralizer to the glucose in the acid-producing fermentation medium is preferably not less than 0.5, and more preferably 0.5-0.7:1.

In a preferred embodiment of the present disclosure, the neutralizer is at least one selected from the group consisting of $CaCO_3$, NaOH and $Ca(OH)_2$, preferably $CaCO_3$.

In the present disclosure, more preferably, the acid-producing fermentation medium comprises, 180-200 g/L of glucose, 9-11 g/L of yeast extract, 1.5-2.5 g/L of sodium acetate, 0.4-0.6 g/L of $KH_2PO_4$, 0.5-1 g/L of $MgSO_4.7H_2O$, 0.1-0.2 g/L of $MnSO_4$, 0.8-1.2 ml/L of Tween 80 and 90-100 g/L of $CaCO_3$, relative to 1 L of the acid-producing fermentation medium. The present disclosure is not limited thereto.

In the present disclosure, the L-lactic acid in the obtained fermentation broth can be separated with the known method, for example, initially removing cells from the fermentation broth, concentrating the fermentation broth after removal of cells to crystallize the product, or with the ion exchange chromatography method or the like.

In the present disclosure, L-lactic acid in the fermentation broth or L-lactic acid separated from the fermentation broth may also be detected with the known method. For example, the yield and optical purity of L-lactic acid can be measured by high performance liquid chromatography and the like.

In a fourth aspect, the present disclosure provides an use of the previously described recombinant strain or an application of the previously described method in the preparation of L-lactic acid or poly(L-lactide).

SEQ ID NO: 11
MKKVNRIAVVGTGAVGTSYCYAMINQGVAEELVLIDINEAKAEGE
AMDLNHGLPFAPTPTRVWKGDYSDCGTADLVVITAGSPQKPGETR
LDLVAKNAKIFKGMIKSIMDSGFNGIFLVASNPVDILTYVTWKES
GLPKEHVIGSGTVLDSARLRNSLSAHFGIDPRNVHAAIIGEHGDT
ELPVWSHTTIGYDTIESYLQKGTIDQKTLDDIFVNTRDAAYHIIE
RKGATFYGIGMSLTRITRAILNNENSVLTVSAFLEGQYGNSDVYI
GVPAVINRQGVREVVEIELNDKEQEQFSHSVKVLKETMAPVL

SEQ ID NO: 12
GeneID: 11173582
ATGAAAAAGGTCAATCGTATTGCAGTGGTTGGAACGGGTGCAGTTG
GTACAAGTTACTGCTACGCCATGATTAATCAGGGTGTTGCAGAAGA
GCTTGTTTTAATCGATATTAACGAAGCAAAAGCAGAAGGGGAAGCC
ATGGACCTGAACCACGCCTGCCATTTGCGCCTACGCCGACCCCGCG
TTTGGAAAGGAGATTATTCCGATTGCGGCACTGCCGATCTTGTTGT
CATTACGGCAGGTTCCCCGCAAAAACCGGGCGAAACAAGGCTTGAT
CTTGTTGCCAAAAACGCAAAAATTTTTAAAGGCATGATTAAGAGCA
TCATGGACAGCGGCTTTAACGGGATTTTTCTTGTTGCCAGCAACCC
GGTTGACATTTTGACATATGTAACTTGGAAAGAGTCCGGCCTGCCG
AAAGAACATGTTATCGGTTCGGGCACAGTGCTTGACTCCGCGCGTC
TCCGCAACTCTTTGAGCGCCCACTTCGGAATTGACCCGCGCAATGT
CCATGCCGCAATTATCGGCGAACACGGCGACACGGAACTTCCGGTT
TGGAGCCATACAACGATCGGTTATGACACCATTGAAAGCTATCTGC
AAAAGGGAACCATTGACCAAAAAACATTAGATGATATTTTTGTCAA
CACGAGAGATGCGGCTTACCATATCATTGAACGAAAAGGGGCCACA
TTTTACGGCATCGGGATGTCTCTGACTCGGATCACAAGAGCGATCC
TGAACAATGAAAACAGTGTTTTGACAGTCTCTGCCTTTTTGGAAGG
CCAGTACGGAAACAGCGATGTGTACATTGGTGTTCCTGCCGTTATT
AACCGCCAAGGCGTCCGTGAAGTGGTTGAAATCGAGCTGAACGACA
AAGAACAGGAACAATTTAGCCATTCTGTTAAAGTATTAAAAGAAAC
GATGGCACCTGTATTGTAA SEQ ID NO: 13
MASITDKDHQKVILVGDGAVGSSYAYAMVLQGIAQEIGIVDIFKDK
TKGDAIDLSNALPFTSPKKIYSAEYSDAKDADLVVITAGAPQKPGE
TRLDLVNKNLKILKSIVDPIVDSGFNGIFLVAANPVDILTYATWKL
SGFPKNRVVGSGTSLDTARFRQSIAEMVNVDARSVHAYIMGEHGDT
EFPVWSHANIGGVTIAEWVKAHPEIKEDKLVKMFEDVRDAAYEIIK
LKGATFYGIATALARISKAILNDENAVLPLSVYMDGQYGLNDIYIG
TPAVINRNGIQNILEIPLTDHEEESMQKSASQLKKVLTDAFAKNDI
ETRQ SEQ ID NO: 14
Gene ID: 31583240
atggcaagtattacggataaggatcaccaaaaagttattctcgttg
gtgacggcgccgttggttcaagttatgcctatgcaatggtattgca
aggtattgcacaagaaatcggatcgttgacattttttaaggacaag
cgaagggtgacgcgattgacttatcgaacgcgctgccattcaccag
cccaaagaagatttattcagctgaatacagcgatgccaaggatgct
gatctggttgttatcactgctggtgctcctcagaagccaggcgaaa
cccgcttggatctggttaacaagaacttgaagatcttgaagtccat
tgttgatccgattgtggattctggctttaacggtatcttcttggtt
gctgccaacccagttgatatcttgacctatgcaacttggaaacttt
ccggcttcccgaagaaccgggttgttggtcaggtacttcattgga
taccgcacgtttccgtcagtccattgctgaaatggttaacgttgat
gcacgttcggtccatgcttacatcatgggtgaacatggtgacactg
aattccctgtatggtcacacgctaacatcggtggcgttactattgc
cgaatgggttaaagcacatccggaaatcaaggaagacaagcttgtt
aagatgtttgaagacgttcgtgacgctgcttacgaaatcatcaaac
tcaaggcgcaaccttctatggtatcgcaactgctttggcacgtat
ctccaaggctatcctgaacgatgaaaatgctgttctgccactgtcc
gtttacatggatggtcaatatggcttgaacgacatctacatcggta
ccccagctgtgatcaaccgaaatggtatccagaacattctggaaat
tccattgaccgaccacgaagaggaatccatgcagaaatctgcttca
caattgaagaaggttctgactgatgccttcgcgaagaacgacatcg
aaacccgtcagtaa SEQ ID NO: 15
MKIIAYGARVDEIQYFKQWAKETGNTLEYHTEFLDEHTVEWAKGFDGIN
SLQTTPYAAGVFEKMHEYGIKFLTIRNVGTDNIDMTAMKKYGIRLSNVP
AYSPAAIAEFALTDTLYLLRNMGKVQAQLHAGDYEKASTFIGKELGQQT
VGVMGTGHIGRVAIKLFKGFGAKVIAYDPYPMKGDHPDFEYVSLEELFK
QSDIIDLHVPGIKQNTHIINEAAFDLMKPGAIVINTARPNLIDTQAMLS
NLKSGKLAGVGIDTYEYETEDLLNLAKHGSFKDPLWDELLAMPNVVLSP
HIAYYTETAVHNMVYFSLONLVDFLTRGETNTEVTAPAK SEQ ID NO: 16
Gene ID: 8422578
ATGAAGATTATTGCATATGGTGCACGCGTGGATGAGATCCAATA
TTTCAAACAGTGGGCTAAGGAAACCGGCAACACGCTGGAATATC
ATACGGAATTTCTTGATGAGCATACCGTTGAATGGGCAAAGGGA
TTTGACGGCATTAACTCACTACAAACGACGCCATACGCAGCTGG
TGTGTTTGAAAAAATGCACGAATATGGCATCAAGTTTCTCACCA
TCCGCAATGTCGGAACCGACAATATCGATATGACGGCGATGAAA
AAATACGGCATTCGCTTAAGTAATGTTCCGGCGTATTCACCGGC -continued

```
TGCCATTGCTGAATTTGCGCTAACCGATACGTTATATCTACTTC

GCAACATGGGAAAGGTTCAAGCACAGCTACATGCAGGCGACTAC

GAAAAAGCCAGCACCTTCATCGGCAAAGAACTTGGTCAGCAAAC

AGTCGGCGTGATGGGGACCGGACACATTGGCCGCGTTGCCATCA

AGCTCTTCAAAGGTTTTGGTGCCAAAGTGATTGCTTACGATCCA

TATCCGATGAAAGGCGATCATCCGGACTTTGAATATGTCAGCTT

GGAAGAACTATTCAAACAAAGTGACATCATTGATCTTCACGTTC

CGGGCATTAAACAAAATACCCACATTATCAACGAGGCCGCGTTT

GATCTTATGAAGCCAGGCGCGATCGTAATTAACACCGCGCGGCC

GAACCTGATTGATACCCAGGCGATGCTCAGCAACCTGAAGTCCG

GTAAACTGGCCGGCGTCGGAATCGATACGTACGAATACGAAACC

GAAGATCTGTTGAACCTCGCCAAACACGGTAGCTTCAAGGATCC

GTTATGGGATGAACTGCTCGCGATGCCAAATGTTGTTCTCAGCC

CGCATATTGCGTACTACACAGAAAACCGCCGTGCACAACATGGT

TTACTTCTCACTGCAGAATTTAGTCGACTTTTTGACAAGGGGAG

AGACGAATACTGAAGTGACAGCACCGGCGAAATAA
```

The present disclosure will be described in detail below with reference to the Examples. The Examples are only for illustrating the present disclosure instead of imposing limitation on the scope of the present disclosure. In the following examples, unless otherwise indicated, the experimental procedures used herein are conventional methods well known among those skilled in the art, and may be performed, for example, using standard procedures described in the following literature: 'Sambrook et al, Molecular Cloning: a Laboratory Manual (the 3$^{rd}$ edition), Cold Spring Harbor Laboratory Press, Cold Spring Harbor, N.Y., USA (2001)'; 'Davis et al, Basic Methods in Molecular Biology, Elsevier Science Publishing, Inc., New York, USA (1995)'; and 'Current Protocols in Cell Biology (CPCB) (Juan S. Bonifacino et al, John Wiley and Sons, Inc.)'.

Unless specifically specified, each of the reagents and culture media used herein was commercially available, and the methods used herein were conventional methods in the art.

The accession number of the recombinant *Lactobacillus rhamnosus* Lr-ALTHT-DBC is CGMCC No. 19507;

The accession number of the recombinant *Lactobacillus rhamnosus* Lr-ALTHT-DLC is CGMCC No. 19508;

1. Culture Medium and Reagents

MRS+CaCO$_3$ plates: MRS solid culture medium+10 g/L CaCO$_3$;

High-sugar MRS+CaCO$_3$ plates: MRS solid culture medium+10 g/L CaCO$_3$+180 g/L glucose;

Screening medium: MRS liquid culture medium+10 g/L CaCO$_3$;

MRS liquid culture medium: 10 g of peptone, 5 g of yeast extract, 10 g of beef extract, 20 g of glucose, 2 g of dipotassium phosphate, 2 g of diammonium citrate, 5 g of anhydrous sodium acetate, 0.25 g of manganese sulfate, 0.58 g of magnesium sulfate, 1 mL of tween 80 and 1,000 mL of distilled water, wherein the pH value was 6.5, and the sterilization was carried out at 121° C. for 20 min;

MRS solid medium: agar was added into above MRS liquid culture medium, wherein the dosage of the agar was 18 g relative to 1,000 mL of distilled water, the pH was adjusted to 6.5, and the sterilization was carried out at 121° C. for 20 min;

Acid-producing fermentation medium: comprising 180 g/L of glucose, 10 g/L of yeast extract, 2 g/L of sodium acetate, 0.5 g/L of KH$_2$PO$_4$, 0.5 g/L of MgSO$_4$.7H$_2$O, 0.2 g/L of MnSO$_4$, and 1 ml/L of tween 80, 90 g/L of CaCO$_3$.

2. The Content of Lactic Acid was Detected by High Performance Liquid Chromatography:

Chromatograph: Agilent Technologies 1260 Infinity II;
Detector: RID;
Separation column: Aminex HPX-87H Column 300×7.8 mm;
Mobile phase: 0.05M sulfuric acid;
Flow rate: 0.5 mL/min;
Sample injection amount: 20 μL;
The retention time of lactic acid was about 14 min.

3. The Contents of Glucose and L-Lactic Acid were Detected by a Biosensor:

Instrument: SBA-40E type biosensor;
Enzyme membrane: D-glucosidase and L-lactate membranes;
sample injection amount: 25 μL.

4. The Optical Purity of Lactic Acid was Detected by High Performance Liquid Chromatography:

Chromatograph: Agilent Technologies 1260 Infinity;
Detector: wavelength 254 nm, sensitivity 0.32 AUFS;
Separation column: MCI GEL-CRS10 W (3 u) 4.6 ID×50 mm;
Mobile phase: 0.002M copper sulfate;
Flow rate: 0.5 mL/min;
Sample injection amount: 20 μL.

The sample was diluted to the total concentration of lactic acid being within a range of 0.5-1 g/L and subjected to detection. The retention time of D-lactic acid was about 11 min, the retention time of L-lactic acid was about 13 min, and the optical purity of the L-lactic acid was calculated according to the peak area.

The glucose-lactic acid conversion rate was calculated by the following formula: total mass of lactic acid at the end of fermentation/initial mass of glucose.

5. RepA mut gene sequence: (SEQ ID NO: 17, the gene sequence after mutation was underlined.)

```
atggctattaaaaatactaaagctagaaattttggattttattata tcctgactcaattcctaatgattggaaagaaaaattagagagtttgg gcgtatctatggctgtcagtcctttacacgatatggacgaaaaaaa gataaagatacatggaataatagtaatattatacaaaatggaaagca ctataaaaaaccacactatcacgttatatatattgcacgaaatcctg taacaatagaaagcgttaggaacaagattaagcgaaaattggggaat agttcagttgctcatgttgagatacttgattatatcaaaggttcata tgaatatttgactcatgaatcaaaggacgctattgctaagaataaac atatatacgacaaaaagatattttgaacattaatgattttgatatt gaccgctatataacacttgatgaaagccaaaaaagagaattgaagaa tttacttttagatatagtggatgactataatttggtaaatacaaaag atttaatggcttttattcgccttaggggagcggagtttggaatttta aatacgaatgatgtaaaagatattgtttcaacaaactctagcgcctt
```

-continued tagattatggtttgagggcaattatcagtgtggatatagagcaagtt atgcaaaggttcttgatgctgaaacgggggaaataaaatga Example 1

Construction of Recombinant Plasmids

Construction of gene knock-out plasmids: the *Escherichia coli* replicon p15Aori (with a sequence derived from commercial vector pACYC), erythromycin resistance gene (with a sequence derived from commercial vector pMG36e), repA mut gene (with a sequence derived from vector pWV01, refer to 'Maguin E[1], Duwat P, Hege T, Ehrlich D, Gruss A, New theromogenic plasmid for gram-positive bacteria, *Journal of bacteriology*, 1992 September; 174(17): 5633-8'; mutant gene sequence (underlined sequence) in repA mut gene were made temperature sensitive) were respectively amplified, and assembled into gene knock-out plasmid pNZ5319TS by using DNA Assembly recombination kit (commercially available from Transgen Corporation). The gene knockout plasmid can be replicated in *Escherichia coli*, cannot be replicated in lactic acid bacteria, and has erythromycin and chloramphenicol resistance genes useful in *Escherichia coli* and *Lactobacillus plantarum*.

Construction of the Gene Substitution Plasmids:

(1) The 1000 bp upstream and downstream sequences of the Gene ldhD (Gene ID: 8422578) to be knocked out were obtained with a PCR method, SacI and SphI enzyme cutting sites (the sequences were amplified from the genome of *Lactobacillus rhamnosus* CGMCC No. 16834) were respectively added simultaneously, and two genes to be substituted were synthesized, namely a BcldhL Gene (the Gene ID: 11173582 sequence was amplified from the genome of *Bacillus coagulans*), and a LcldhL Gene (the Gene ID: 31583240 sequence was amplified from the genome of *Lactobacillus casei*).

(2) The upstream amplification fragment of ldhD, the BcldhL gene fragment or the LcldhL gene fragment, and the downstream amplification fragment of ldhD were sequentially connecting by using an overlapping extension amplification method, in order to obtain the to-be-substituted fragments ldhD-BcldhL and ldhD-LldhL.

(3) A fragment of a gene to be inserted was obtained by using the double enzyme digestion with SacI and SphI; the previously constructed pNZ5319TS plasmid was also subjected to the double enzyme digestion with SacI and SphI to obtain a fragment having the chloramphenicol resistance gene.

(4) The vector and the gene fragment both subjected to the same double enzyme digestion and purification were connected to obtain the gene substitution plasmid. The gene substitution plasmid can be replicated in *Escherichia coli*, cannot be replicated in lactic acid bacteria, and had a chloramphenicol resistance gene useful in *Escherichia coli* and *Lactobacillus rhamnosus*. In order to substitute the ldhD gene with BcldhL gene of *Bacillus coagulans* and LcldhL gene of *Lactobacillus casei*, two gene substitution plasmids pNZ5319TS-ldhD-BcldhL and pNZ5319 TS-ldhD-LldhL were respectively constructed.

Amplification of the ldhD-BcldhL Fragment:
ldhD-BcldhL-up-F (SEQ ID No. 1)
ATGAGCTCGGCACCTTGAACAGTGTAACCA ldhD-BcldhL-up-R:

(SEQ ID No. 2)
CCACTGCAATACGATTGACCTTTTTCATATTCTCAATATC

TCCTTGATTTCGATTTGTCC ldhD-BcldhL-bc-F (SEQ ID No. 3)
GGACAAATCGAAATCAAGGAGATATTGAGAATATGAAAA

AGGTCAATCGTATTGCAGTGG ldhD-BcldhL-bc-R:

(SEQ ID NO. 4)
TGCTTATTTTTGCAGCTTAAAGGATCCTTACAATACAGG

TGCCATCGTTTCTTTT ldhD-BcldhL-down-F (SEQ ID NO. 5)
AAAAGAAACGATGGCACCTGTATTGTAAGGATCCTTTAA

GCTGCAAAAATAAGCA ldhD-BcldhL-down-R:

(SEQ ID NO. 6)
ATGCATGC AGA CTC AGC TCT TGG CGG CCT TT

Amplification of ldhD-LcldhL Fragment
ldhD-LldhL-up-F (SEQ ID NO. 1)
ATGAGCTCGGCACCTTGAACAGTGTAACCA ldhD-LldhL-up-R:

(SEQ ID NO. 7)
GGTGATCCTTATCCGTAATACTTGCCATATTCTCAATA

TCTCCTTGATTTCGATTTGTCC ldhD-LcldhL-lc-F (SEQ ID NO. 8)
GGACAAATCGAAATCAAGGAGATATTGAGAATATGGCA

AGTATTACGGATAAGGATCACC ldhD-LcldhL-lc-R:

(SEQ ID NO. 9)
TGCTTATTTTTGCAGCTTAAAGGATCCTTACTGACGG

GTTTCGATGTCGTTCT ldhD-LldhL-down-F (SEQ ID NO. 10)
AGAACGACATCGAAACCCGTCAGTAAGGATCCTTTAA

GCTGCAAAAATAAGCA ldhD-LldhL-down-R:

(SEQ ID NO. 6)
ATGCATGC AGA CTC AGC TCT TGG CGG CCT TT

Example 2

1) Homologous Recombination of Strains:

Electrotransformation scheme of the *Lactobacillus rhamnosus*: a single colony of a plate-activated *Lactobacillus rhamnosus* CGMCC No. 16834 (Lr-ALHTT) was inoculated to 4 mL of MRS culture medium for overnight cultivation at 37° C., the single colony was transferred to 100 mL of MRS culture medium containing 1% glycine according to the initial $OD_{600}$=0.2, and subjected to shaking cultivation at 37° C. until $OD_{600}$=0.6; the bacterial liquid was subjected to ice bath at 4° C. for 20 min, and subjected to centrifugation at 8000×g for 15 min to collect thalli; the cells were washed with 100 mL of 1 mM $MgCl_2$ pre-cooled at 4° C. and 30% PEG 1000 each for 1 time sequentially; the thalli were re-suspended in 1 mL of 30% PEG1000 pre-cooled at 4° C., each unit was loaded with 100 μL thalli with competent state. 1-5 μg of the corresponding gene substitution plasmid prepared in Example 1 was added to each unit of thalli with competent cell, and subjected to ice bath for 10 min, and then applied to a 0.2 cm electric rotor, and applied with 1.75-2 kV electric shock, 0.8 mL of MRS-SM culture medium (0.5M sucrose and 0.1M $MgCl_2$ were added to the MRS culture medium) was rapidly added thereto, and the thalli were resuscitated and cultured at 37° C. for 2 h, and subsequently centrifuged for 1 min, a portion of the supernatant was removed and the filtrate was re-suspended and coated on the MRS plates containing the corresponding antibiotics, and cultured at 42° C. for 3 days to obtain the single colonies.

2) Strain Lr-ALTHT-DBC and Strain Lr-ALTHT-DLC

Preparation of the Lr-ALTHT-DBC gene substitution strain: the gene substitution plasmid pNZ5319TS-ldhD-BcldhL obtained in the Example 1 was transferred into a *Lactobacillus rhamnosus* Lr-ALHTT, and subjected to cultivation by 15 μg/ml chloramphenicol at 42° C. and screening to obtain the positive transformants, 1-2 positive transformants were selected and subcultured in a MRS liquid culture medium which did not contain resistance for screening out the strains exchanged for the second time, it was confirmed by the colony PCR and sequencing that the ldhD gene has been substituted with the BcldhL gene, such that the recombinant *Lactobacillus rhamnosus* Lr-ALHTT-DBC was obtained.

Preparation of the Lr-ALTHT-DLC gene substitution strain: the gene substitution plasmid pNZ5319TS-ldhD-LcldhL obtained in the Example 1 was transferred into a *Lactobacillus rhamnosus* Lr-ALHTT, and subjected to cultivation by 15 μg/ml chloramphenicol at 42° C. and screening to obtain the positive transformants, 1-2 positive transformants were selected and subcultured in a MRS liquid culture medium which did not contain resistance for screening out the strains exchanged for the second time, it was confirmed by the colony PCR and sequencing that the ldhD gene has been substituted with the LcldhL gene, such that the recombinant *Lactobacillus rhamnosus* Lr-ALHTT-DLC was obtained.

Example 3

L-Lactic Acid Produced by Fermentation of Recombinant Strain

The single colonies of the recombinant *Lactobacillus rhamnosus* Lr-ALHTHT-DBC and Lr-ALHTHT-DLC obtained in Example 2 were respectively inoculated in an MRS culture medium, and subjected to cultivation overnight at 37° C. and rotational speed 150 rpm to obtain a recombinant *Lactobacillus rhamnosus* Lr-ALHTHT-DBC seed solution and a recombinant *Lactobacillus rhamnosus* Lr-ALHTHT-DLC seed solution, each having an $OD_{600}$ of 12. The seed solutions were subsequently inoculated into 200 mL of an acid-producing fermentation medium in a proportion of 10% (v/v), the mixture was subjected to shaking cultivation at 37° C. and 150 rpm for 6 hours to allow the strains to grow, then the temperature was raised to 48° C. and the mixture was further subjected to shaking cultivation at 150 rpm for 42 hours to obtain a fermentation broth (the total fermentation time was 48 hours). After the fermentation was finished, the total yield of the lactic acid and the optical purity of the L-lactic acid were measured by using the high performance liquid chromatography.

As a result, when the *Lactobacillus rhamnosus* Lr-ALHTT-DBC and the *Lactobacillus rhamnosus* Lr-ALHTT-DLC were fermented at 48° C. under the shake flask of 200 mL, the lactic acid contents in the fermentation liquor obtained by fermenting the recombinant *Lactobacillus rhamnosus* Lr-ALHTT-DBC and the recombinant *Lactobacillus rhamnosus* Lr-ALHTT-DLC for 48 h were 216 g/L and 215.3 g/L respectively, the glucose-lactic acid conversion rates were 97% and 96.5%, and the optical purities of the L-lactic acid were 99.8% and 99.5%.

Comparative Example 1

Lactic acid was produced by fermentation according to the method of Example 3 except that the recombinant *Lactobacillus rhamnosus* Lr-ALHTT-DBC (or Lr-ALHTT-DLC) was substituted with the starting strain *Lactobacillus rhamnosus* with accession number of CGMCC No. 16834 (Lr-ALHTV);

The results shown that the content of lactic acid in the obtained fermentation broth was 157 g/L, and the optical purity of L-lactic acid was 99%.

The optical purity of the products of the recombinant strains Lr-ALHTT-DBC and Lr-ALHTT-DLC reaches 99.5%, and provides another option which can meet the industrial requirements. As can be seen by comparing the Example 3 with the Comparative Example 1, the lactic acid produced by recombinant strain obtained by genetic modification of the Gene knock-out of D-lactate dehydrogenase (ldhD) of the starting strain *Lactobacillus rhamnosus* with accession number of CGMCC No. 16834 by using BcldhL Gene of *Bacillus coagulans* (Gene ID: 11173582, amplified from the genome of *Bacillus coagulans*) and LcldhL Gene of *Lactobacillus casei* (Gene ID: 31583240, amplified from the genome of *Lactobacillus casei*) by using the method of the present disclosure can produce more remarkably improved fermentation effect, the lactic acid contents in the obtained fermentation broth can reach 216 g/L and 215.3 g/L respectively, the glucose-lactic acid conversion rates are 97% and 96.5% respectively, and the optical purities of L-lactic acid are 99.8 and 99.5% respectively, so that the yield of L-lactic acid and the optical purity of the product L-lactic acid are significantly improved.

INDUSTRIAL APPLICABILITY

The aforementioned researches show that the recombinant strains Lr-ALHTT-DBC and Lr-ALHTT-DLC are superior to the starting strain *Lactobacillus rhamnosus* Lr-ALHTT in the aspects of L-lactic acid yield and optical purity for the product, thus the present disclosure provides a novel production strain which is environment-friendly and has low fermentation cost, high production speed of the L-lactic acid and high optical purity of the product, and provides an optimal potential choice for industrial microbial fermentation and production of the L-lactic acid.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A recombinant strain for producing L-lactic acid, wherein the recombinant strain is obtained by genetically modifying a starting strain that is *Lactobacillus rhamnosus* with accession number of CGMCC No. 16834, the activity of D-lactate dehydrogenase of the recombinant strain is weakened or inactivated, and the activity of L-lactate dehydrogenase is enhanced, as compared with the starting strain;
  wherein a D-lactate dehydrogenase gene in the recombinant strain is knocked out wherein the amino acid sequence encoded by said D-lactate dehydrogenase gene is SEQ ID NO: 15;
  the recombinant strain comprises a L-lactate dehydrogenase gene encoding the amino acid sequence of SEQ ID NO: 11 and/or SEQ ID NO: 13; wherein said recombinant strain has an accession number of CGMCC No. 19507 or CGMCC No. 19508.

2. The recombinant strain of claim 1, wherein the sequence of the knocked-out D-lactate dehydrogenase gene is as set forth as SEQ ID NO: 16.

3. The recombinant strain of claim 1, wherein the recombinant strain comprises a L-lactate dehydrogenase gene, wherein the L-lactate dehydrogenase gene comprises a nucleotide sequence as set forth as SEQ ID NO: 12 and/or SEQ ID NO: 14.

* * * * *